US011903926B1

(12) United States Patent
Knobler

(10) Patent No.: US 11,903,926 B1
(45) Date of Patent: *Feb. 20, 2024

(54) NON-HORMONAL TREATMENT OF HOT FLASHES

(71) Applicant: Iris International Pharma, LLC, Fort Washington, PA (US)

(72) Inventor: Robert L. Knobler, Fort Washington, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/390,276

(22) Filed: Apr. 22, 2019

Related U.S. Application Data

(63) Continuation-in-part of application No. 15/447,675, filed on Mar. 2, 2017, and a continuation-in-part of application No. 14/245,509, filed on Apr. 4, 2014, now Pat. No. 9,468,631, and a continuation-in-part of application No. 13/411,660, filed on Mar. 5, 2012, now Pat. No. 9,616,123.

(51) Int. Cl.
| | |
|---|---|
| *A61K 31/4045* | (2006.01) |
| *A61K 31/343* | (2006.01) |
| *A61K 31/427* | (2006.01) |
| *A61K 31/451* | (2006.01) |
| *A61K 9/00* | (2006.01) |
| *A61K 31/5415* | (2006.01) |

(52) U.S. Cl.
CPC ........ *A61K 31/4045* (2013.01); *A61K 9/0053* (2013.01); *A61K 9/0073* (2013.01); *A61K 31/343* (2013.01); *A61K 31/427* (2013.01); *A61K 31/451* (2013.01); *A61K 31/5415* (2013.01)

(58) Field of Classification Search
CPC .............. A61K 31/4045; A61K 31/343; A61K 31/427; A61K 31/5415; A61K 9/0053; A61K 31/451; A61K 9/0073
USPC ....................................................... 514/362
See application file for complete search history.

(56) References Cited

U.S. PATENT DOCUMENTS

| | | | | |
|---|---|---|---|---|
| 9,468,631 B1 * | 10/2016 | Knobler | ................. | A61P 15/12 |
| 9,616,123 B1 * | 4/2017 | Knobler | ................. | A61K 45/06 |
| 9,693,993 B1 * | 7/2017 | Knobler | ............... | A61K 31/381 |
| 10,806,722 B1 * | 10/2020 | Knobler | ............... | A61K 31/404 |

OTHER PUBLICATIONS

Zichella et al. in Maturitas 8, 229-237 (1986) (Year: 1986).*
Hoffman et al. in Psychopharmacology 107:277-284 (1992) (Year: 1992).*
Editorial Review in Diabetes Care 34, 789-794 (2011) (Year: 2011).*
Cornell et al. in www.pharmacytimes.com/publications/issue /2010/December2010/Novel-Treatment-for-the-Management-of-Type-2-Diabetes-in-Adults (retrieved from the internet Dec. 12, 2014) (Year: 2010).*
Brooks, DJ in Journal of Neurology, Neurosurgery and Psychiatry 68: 685-690 (2000) (Year: 2000).*
Korczyn et al. in Neurology 53(2):364-370 (1999) (Year: 1999).*
Knobler (Menopause, (Nov.-Dec. 2010) vol. 17, No. 6, p. 1231. Abstract No. P-30; Meeting Info: 21st Annual Meeting of the North American Menopause Society. Chicago, IL, United States. Oct. 6, 2010-Oct. 9, 2010 (Year: 2010).*

* cited by examiner

*Primary Examiner* — Yevgeny Valenrod
(74) *Attorney, Agent, or Firm* — Andrew L. Salvatore, Esquire

(57) ABSTRACT

The subject invention describes the use of dopamine agonists with affinity for the dopamine $D_2$, $D_3$, or $D_4$ receptors (the $D_2$ family) for treatment of hot flashes, regardless of their being caused by natural aging in women or medical/surgical intervention of the HPG axis in either sex. The $D_2$ family of dopamine receptors is most responsive to $D_2$ agonist molecules, but also responsive to multiple other molecules that directly or indirectly utilize this pathway. Alpha-2-adrenergic agonists act synergistically to further reduce the frequency and severity of hot flashes and prolong the duration of dosing effectiveness. The combination of a $D_2$ family dopamine agonist and alpha-2-adrenergic agonist, as well as additional molecules that can utilize the $D_2$ receptor family pathway through formation of heterodimers, permits a multitude of molecules of varying efficacy for the treatment of hot flashes in either women or men. The subject invention expands the available non-hormonal options for treatment of hot flashes that are otherwise most disruptive to normal activities of daily living.

2 Claims, 3 Drawing Sheets

NON-HORMONAL TREATMENT OF HOT FLASHES

CROSS REFERENCE TO RELATED APPLICATIONS

This application is a continuation in part application of, and claims priority to, U.S. patent application Ser. No. 13/411,660 filed on Mar. 5, 2012, U.S. patent application Ser. No. 14/245,509 filed on Apr. 4, 2014, and U.S. application Ser. No. 15/447,675 filed on Mar. 2, 2017. The above referenced prior applications are hereby incorporated herein by reference.

TECHNICAL FIELD

The subject invention relates to treatments and treatment methods of hot flashes. Hot flashes may be caused by menopause and they may be caused by various methods of treatment of diseases and conditions which share a common biochemical pathway, the hypothalamic-pituitary-gonadal (HPG) axis. The subject invention exploits the HPG neurochemical pathway for use in the non-hormonal treatment of hot flashes. The HPG axis pathway is present in both women and men, and the treatment simulates naturally occurring neurotransmitters to control hot flashes in both men and women.

BACKGROUND OF THE INVENTION

Under normal circumstances, a signal from the brain, mediated through the hypothalamus, discharges gonadotropin releasing hormone (GnRH). This leads to the subsequent release of hormones that have direct actions on the gonads of either sex. They are LH, luteinizing hormone and FSH, follicle stimulating hormone. LH leads to the production of estrogen in the ovaries of the female, and testosterone in the testes of the male. There is a difference in the cadence of release of these molecules that is characteristic for either sex. In females, the release of LH is pulsatile and fluctuates throughout the menstrual cycle, while in males, the release is tonic. FSH, follicle stimulating hormone, affects each sex as well. It leads to maturation of the ovarian follicle and also contributes to the production of progesterone in the female, which is impacted by whether pregnancy occurs. In the male, FSH supports the development of sperm. Hormones produced within the ovaries or testes then act upon the hypothalamus, completing the HPG axis circuit, and acting in a feedback loop to regulate hormone levels within a predictable range during the reproductive years. In females, with the onset of menopause, there is a decline in the production of estrogen, and these effects carry over to the remaining steps within the HPG axis. There is an increase in GnRH, LH and FSH during this phase (See FIGS. 1 and 2). This is accompanied by the onset of hot flashes.

Hot flashes, regardless of cause, are characterized by bursts of vasomotor symptoms that vary in frequency and intensity. In women undergoing menopause, hot flashes reflect a reduction in estrogen associated with normal aging. This leads to disruption of the normally synchronized menstrual cycle. This change is associated with dysregulated pulses of activity within the HPG axis. The hot flashes are often associated with sleep disturbances and other symptoms. Hormone replacement therapy (HRT) has previously been suggested, utilized, and is therapeutically effective. Unfortunately, HRT has been demonstrated to increase the risk of vascular and malignant disease. An effective non-hormonal method of relieving hot flashes has long been sought to remedy this dilemma.

There are both hormonal and non-hormonal methods in which to influence the integrity of the HPG axis and impact hot flashes. Although the precise mechanism of hot flashes is not firmly established, it has been empirically confirmed that they most typically occur following the decline in the regulatory signal in the HPG axis impacting GnRH, LH and FSH release.

Hot flashes are an important cause of discomfort and distress to affected individuals. In women, hot flashes represent a decline in available estrogen which most commonly occurs in the context of normal aging (menopause). This condition affects millions of women each year.

Hot flashes may also occur in both men or women under other circumstances as well. This can include the surgical removal of the ovaries, which rapidly eliminates the primary source of estrogen. In other circumstances, adjunctive hormonal manipulation, such as that utilized in the treatment of sex hormone-sensitive malignant diseases, also eliminates endogenous sex hormone activity. The latter groups can include breast cancer in women and prostate cancer in men, which each also affect significant numbers of individuals annually. Hot flashes as a consequence of this form of adjuvant therapy can impede compliance with treatment, putting these individuals at increased risk from their primary disease.

For instance, in women, hot flashes frequently are associated with the therapeutic delivery of selective estrogen receptor modulators (SERMs), such as tamoxifen. This treatment is utilized in pre-menopausal women with hormone-dependent breast, ovarian or uterine cancer. This limits the efficacy of circulating estrogen, effectively producing an estrogen deficiency state which leads to hot flashes. Hot flashes may also follow the use of medication to block the enzyme (aromatase), essential for the synthesis of estrogen. There are several aromatase inhibitors (anastrozole, exemestane and letrozole amongst others), which are used in post-menopausal women with hormone-dependent breast, ovarian or uterine cancer. These molecules are also considered for the treatment of infertility, precocious puberty, endometriosis, gynecomastia, uterine fibroids, precocious puberty and other conditions. In these instances hot flashes are the direct result of reduced production of estrogen, which can be measured in the circulation.

In men, hot flashes occur when receiving hormone-altering treatments to interfere with androgen (testosterone) production, as in the treatment of prostate cancer. This may include radical therapies, such as castration (orchiectomy), or by desensitizing the GnRH receptors, and thereby reduce hormone production. There is a large group of agents utilized to interrupt the production or action of testosterone in the treatment of prostate cancer. These include GnRH agonists or analogues such as, leuprolide, goserelin and triptorelin; GnRH blocking agents (degarelix) to impede testosterone release; anti-androgens (bicalutamide, flutamide, nilutamide), which block the action of testosterone on prostate cancer cells; abiraterone, to block the synthesis of androgen; and, enzalutamide, to block androgen receptor signaling. The results of treatment with these molecules reduces testosterone which leads to an increase in hot flashes.

Various methods have been used to treat hot flashes in the past but these treatment methods have proven to be inadequate due to their lack of efficacy or dangers associated with side effects to the treatment. Hormonal Replacement Therapy (HRT) is a form of treatment which supplements naturally occurring hormones in the body. HRT treatment aims to supplement levels of estrogen and progestin to reduce levels of LH and FSH and thus reduce menopausal symptoms. However, HRT brings with it the risk of a number of other health risks including cancer, heart attack, and strokes.

Hot flashes have also been treated with serotonin re-uptake inhibitors (SSRIs). SSRIs increase levels of serotonin by inhibiting its re-uptake into presynaptic cells. In theory, by increasing the levels of serotonin in the brain, the claimed benefits achieved as an anti-depressant, i.e. improving mood and promoting sleep, also serve to alleviate hot flashes. However, the efficacy of SSRIs has been disputed.

Selective Estrogen Receptor Modulators (SERMs) are another category of drugs which have been used to treat hot flashes. These drugs act as agonists or antagonists to estrogen receptors throughout the body. However, it has been reported that most SERMs actually increase hot flashes.

Other drugs such as anti-seizure medications (i.e., gabapentin), and blood pressure medications (i.e., clonidine), have also been used to treat hot flashes. The mechanism of action of these agents is poorly understood, and the effectiveness of these treatments is disputed. Accordingly, there remains the need for an effective and safe treatment to reduce the incidence of hot flashes.

The subject invention provides a non-hormonal method for a safe and effective treatment strategy in the control of hot flashes. Because the component steps within the HPG axis that regulate GnRH are identical in the two sexes, this method is equally applicable to both women and to men. The invention utilizes non-hormonal molecules, which mimic the activity of the hormones and selectively interact with the HPG axis to regulate hot flashes under the varied circumstances noted. The invention, therefore, provides a safe, effective method which overcomes the limitations of the prior art with the benefit of facilitating compliance to adjunctive chemotherapy.

SUMMARY OF THE INVENTION

The present invention is based upon a common mechanism of action utilizing non-hormonal treatments, acting through the HPG axis to control hot flashes. This treatment exploits the $D_2$ family of dopamine receptors as the desired therapeutic target. The $D_2$ family of receptors includes $D_2$, $D_3$ and $D_4$ receptors. The $D_2$ receptor exists in two isoforms, the $D_{2\ short}$ ($D_{2s}$) and the $D_{2\ long}$ (DA). The $D_{2s}$ is notably represented within the hypothalamus. The $D_2$ receptor family members may be effective in this capacity through interaction with relevant molecules acting exclusively on any one of these receptors, utilizing specific dopamine agonists. The effectiveness of this interaction may be enhanced through the synergistic effect of the addition of a selective alpha-2-agonist.

The present invention exploits the ability of molecules interacting with the $D_2$ receptor family in a promiscuous manner, to form a new entity, a heterodimer. Through formation of heterodimers, ligands which bind to receptors other than members of the $D_2$ family of receptors, such as $D_1$, $5HT1_B$, alpha-2A-adrenergic receptors, can and do interact in a novel manner. Specifically, a heterodimer receptor composed in part by the $D_1$ receptor and in part by the $D_2$ receptor, a $D_1$-$D_2$ heterodimer, serves as an example.

The heterodimer that is formed, depending upon its properties, allows binding of a ligand that would not otherwise interact or be anticipated to influence the $D_2$ receptor family member to yield a therapeutic response. This has broad implications in understanding the scope of effectiveness of molecules known to reduce hot flashes and in the design of new effective ligands.

These molecules having diverse compositions, nonetheless, have wide ranging use in both men and women in the relief of hot flashes, whether caused by natural events of aging (menopause), surgical removal of the ovaries or the consequence of adjuvant hormone therapy. These latter circumstances extend beyond the scope of vasomotor symptoms of menopause but nonetheless contribute to symptoms of hot flashes which are effectively treated by targeting the HPG axis specifically through the $D_2$ receptor family. This invention fulfills a long standing need for addressing a very common problem and will also aide individuals in tolerating adjunctive therapies for the treatment of hormone-driven malignancies such as breast cancer in women or prostate cancer in men.

DETAILED DESCRIPTION OF THE INVENTION

The present invention is based upon a common mechanism of action utilizing non-hormonal treatments, acting through the HPG axis to control hot flashes. This treatment exploits the $D_2$ family of dopamine receptors as the desired therapeutic target. The $D_2$ family of receptors includes $D_2$, $D_3$ and $D_4$ receptors. The $D_2$ receptor exists in two isoforms, the $D_{2\ short}$ ($D_{2s}$) and the $D_{2\ long}$ (DA). The $D_{2s}$ is notably represented within the hypothalamus. The $D_2$ receptor family members may be effective in this capacity through interaction with relevant molecules acting exclusively on any one of these receptors, utilizing specific dopamine agonists. The effectiveness of this interaction may be enhanced through the synergistic effect of the addition of a selective alpha-2-agonist.

Figure 1:
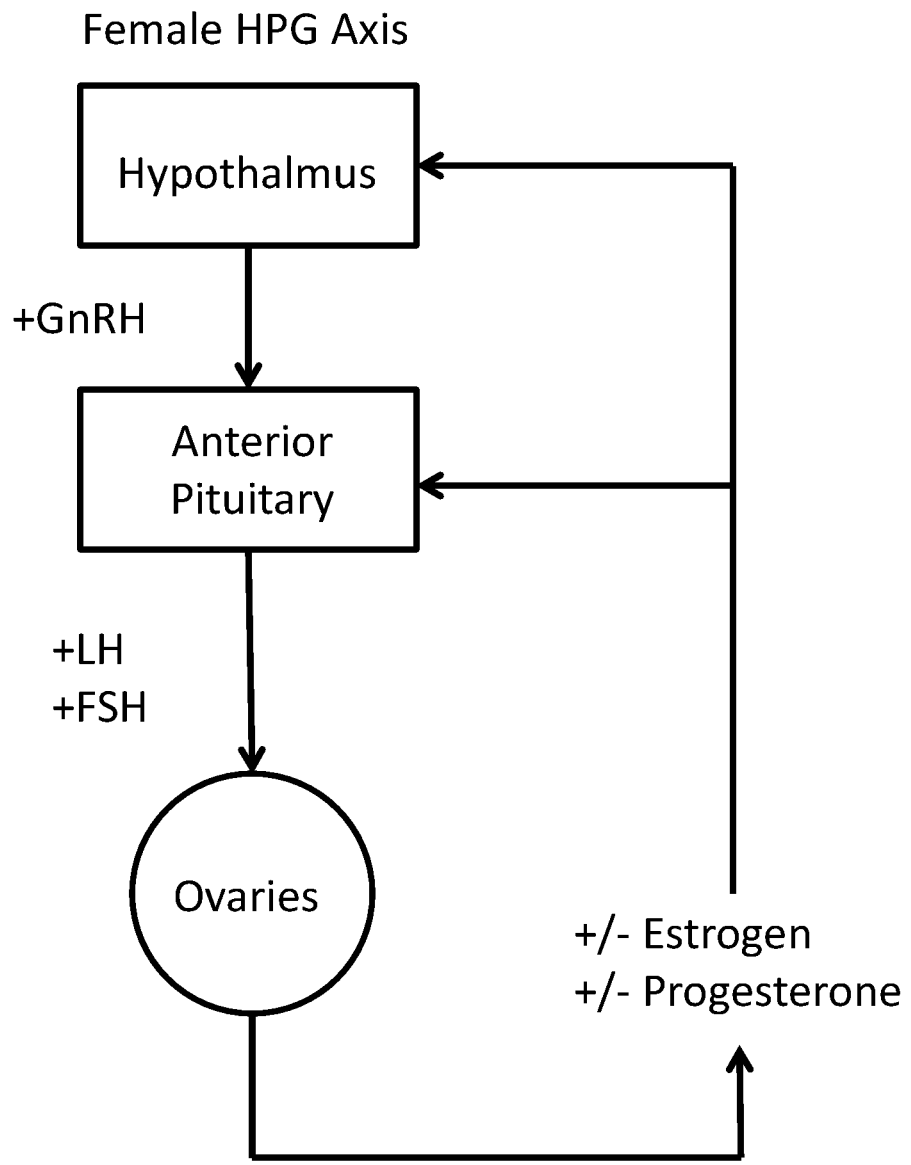
FIG. 1 shows a flowchart of the female hypothalamic-pituitary-gonadal axis hormonal feedback pathway.
Figure 2:
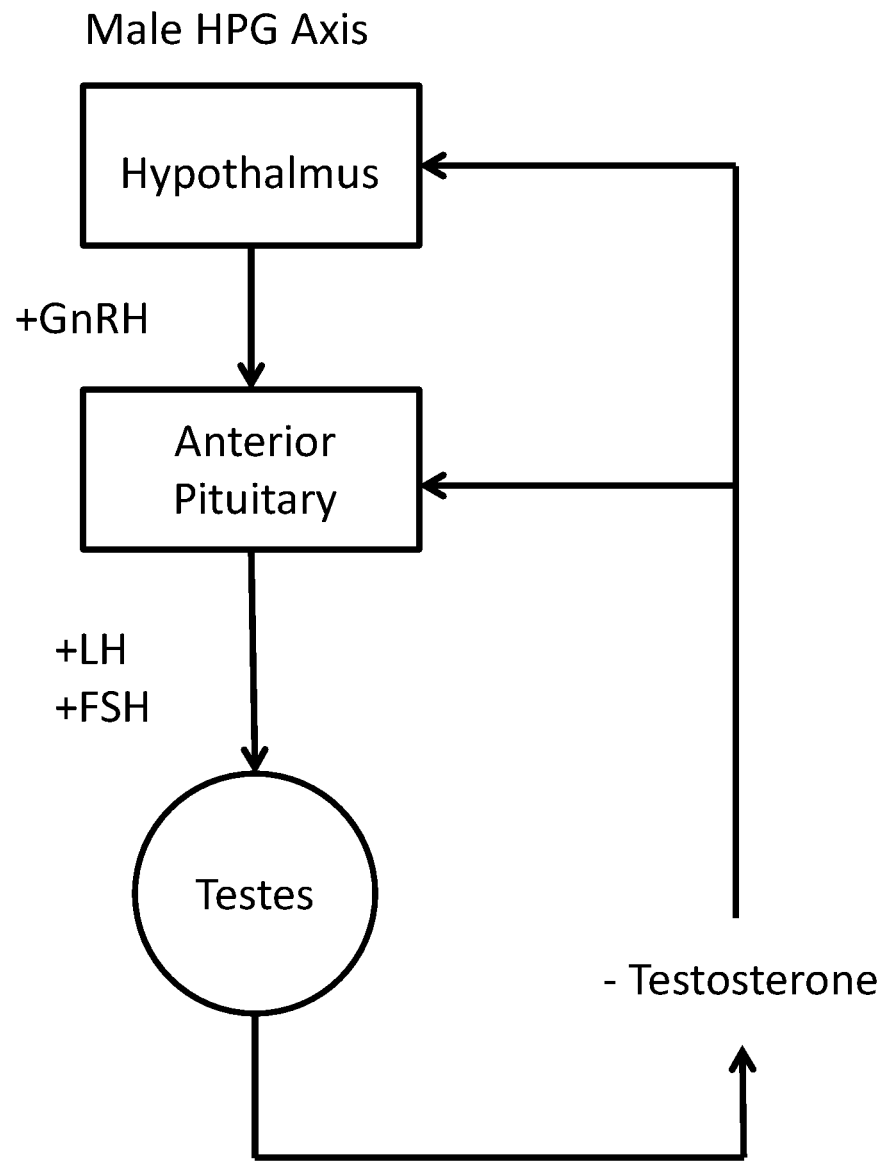
FIG. 2 shows a flowchart of the male hypothalamic-pituitary-gonadal axis hormonal feedback pathway.
Figure 3:
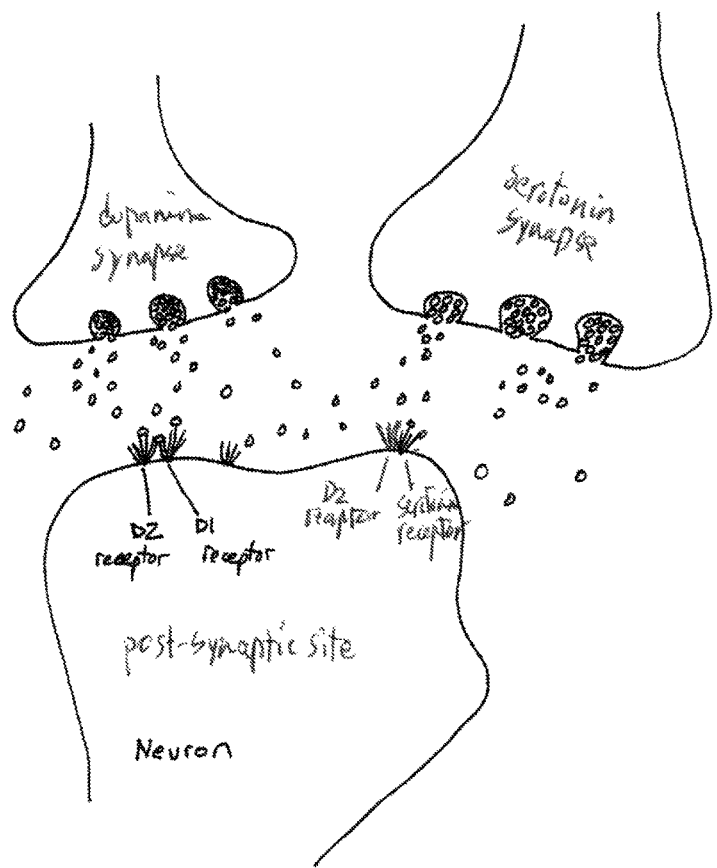
FIG. 3 shows the interaction of various neurotransmitters from different presynaptic neurons on the various receptors of a target neuron.

The present invention exploits the ability of molecules interacting with the $D_2$ receptor family in a promiscuous manner, to form a new entity, a heterodimer. Predictably, this method yields a graded response. Through formation of heterodimers, ligands which bind to receptors other than members of the $D_2$ family of receptors, such as $D_1$, $5HT1_B$, alpha-2A-adrenergic receptors, can and do interact in a novel manner. Specifically, a heterodimer receptor composed in part by the $D_1$ receptor and in part by the $D_2$ receptor, a $D_1$-$D_2$ heterodimer, serves as an example. FIG. 3 illustrates how molecules may interact with more than one receptor and function as a heterodimer. Presynaptic neurons release neurotransmitters or hormones which act as signals to activate or inhibit receptors on target neurons. The hormonal signals may bind to a specific receptor on the target neuron to produce a neuronal response. However, hormonal signals may interact with various receptor types and may interact with different families of receptors, for example, $D_1$ and $D_2$ receptors forming a heterodimer between the two receptors. In this manner, neurotransmitter molecules which would not typically interact with the $D_2$ receptor, may influence the neuronal response through interaction with the $D_2$ receptor as a heterodimer. The neurotransmitter molecules which have the greatest impact on the $D_2$ receptor family will have the greatest effect on the HPG axis to reduce hot flashes.

The prior art does not address the effect of molecular stimulation of the $D_2$ receptor family, alone or in combination with other receptors as a heterodimer, to reduce hot flashes. This analysis demonstrates that a positive response, of reduced hot flash frequency and intensity, is graded and dependent on the ligand evaluated. This distinction is based upon recognition of the breadth of effective molecules utilized, and the neuro-regulatory circuit impacted. The present invention provides a new, non-hormonal method for regulation of hot flashes in multiple clinical settings based upon the site of action, the HPG axis, and not confined to a specific compound.

The heterodimer that is formed, depending upon its properties, allows binding of a ligand that would not otherwise interact or be anticipated to influence the $D_2$ receptor family member. In this way, molecules, not otherwise anticipated to impact the $D_2$ receptor family, can bind and yield a therapeutic response. This has broad implications in understanding the scope of effectiveness of molecules known to reduce hot flashes and in the design of new effective ligands.

As noted above, hot flashes may naturally be caused in women. This is through the aging process during which estrogen levels become reduced, leading to hot flashes. However, hot flashes may also be caused in men and women by treatment of other diseases or conditions which are hormone dependent, for example in treatment of hormone-dependent cancers. The subject invention seeks to reduce the effect of hot flashes by targeting the HPG axis, specifically through the $D_2$ receptor family. Therefore, molecules with relevant specific activity at the $D_2$ receptor family are active and effective in reducing hot flashes. Additionally, molecules are also effective, in a graded response, based upon the formation of heterodimers with the $D_2$ family of receptors. There are many possible combinations, due to the promiscuous nature of the $D_2$ receptor family properties. The affinity of the specific ligand molecule and the unique heterodimer formed will determine the degree of response generated in the regulation of hot flashes.

Pramipexole (Mirapex) is listed as an example of a $D_2$ family receptor agonist (binding to $D_2$, $D_3$ or $D_4$ receptors) in blocking hot flashes, including vasomotor symptoms of menopause. Pramipexole (Mirapex) combined with an alpha-2-agonist (e.g. tizanidine or clonidine), has enhanced activity in blocking hot flashes, including vasomotor symptoms of menopause and it has been clinically shown that the beneficial effect of the $D_2$ receptor family agonist and the alpha-2-agonist together are enhanced such that they synergistically work together to reduce hot flash frequency and intensity. The combined agents provide a longer duration of effect.

Based upon the observed unique activity of all $D_2$ (binding to $D_2$, $D_3$ or $D_4$ receptors) family members tested, i.e., ropinirole, pramipexole, rotigotine and piribedil, in controlling hot flashes to date, including vasomotor symptoms of menopause, the evidence documents that any current or future $D_2$ family (binding to $D_2$, $D_3$ or $D_4$ receptors) agonist, either individually or in combination with a synergistic alpha-2-agonist, is effective in controlling hot flashes, including vasomotor symptoms of menopause.

Finally, based upon the observations, ligand molecules unrelated to the specific $D_2$ family of receptors (e.g., paroxetine, venlafaxine, etc.) are effective in a graded manner for use in the relief of hot flashes, including vasomotor symptoms of menopause consistent with indirect activity at the $D_2$ family ($D_2$, $D_3$ or $D_4$) of receptors through heterodimer formation (FIG. 3).

These ligand molecules having diverse compositions, nonetheless, have wide ranging use in both men and women in the relief of hot flashes, whether caused by natural events of aging (menopause), surgical removal of the ovaries or the consequence of adjuvant hormone therapy. These latter circumstances extend beyond the scope of vasomotor symptoms of menopause but nonetheless contribute to symptoms of hot flashes which are effectively treated by targeting the HPG axis specifically through the $D_2$ receptor family. This invention fulfills a long standing need for a very common problem, and will also aide individuals in tolerating adjunctive therapies for the treatment of hormone-driven malignancies such as breast cancer in women or prostate cancer in men.

Clinical Studies

Clinical studies clearly show that when treating menopausal symptoms in women, a variety of molecules with $D_2$ receptor family activity ($D_2$, $D_3$, or $D_4$ dopamine agonists), especially when combined with an alpha-2-adrenergic agonist, provide excellent control of menopausal symptoms including hot flashes. Case studies of four different women were conducted by treating them with ropinirole (an $D_2$ receptor family dopamine agonist) and tizanidine (an alpha-2-adrenergic agonist). The efficacy of the $D_2$ agonist alone to treat hot flashes was demonstrated through the studies. Relief from hot flashes was further enhanced through additional treatment with the alpha-2-adrenergic agonist. The combination provided extended duration of clinical benefit.

The patients were treated by escalating the dose of ropinirole to 4 mg, testing the hypothesis of a dopaminergically regulated pathway within the central nervous system which impacts hot flashes. The dopaminergic agonist ropinirole was escalated from an initial dose of 0.25 mg to a final dose of 4 mg at bedtime without side effects and with the dramatic shutdown of previously intolerable hot flashes of menopause.

The first woman, JK, a 58-year-old woman, began experiencing symptoms of insomnia and had initially been placed on low dose Hormone Replacement Therapy (HRT) without benefit on her sleep cycle. Despite two changes in dose and formulation of HRT, no significant benefit in sleep cycle was realized. Neither were efforts to treat her sleep problems with standard sedative hypnotics such as zolpidem, zaleplon, temazepam or clonazepam. Hot flashes then began, and became both more frequent and more intense. These were characterized by severe flushing of the face and upper chest with drenching sweats. Each hot flash would typically last 30-90 seconds and was accompanied by an intense sensation of heat. The hot flash would then rapidly subside with a sense of being chilled, reflecting the normal physiologic function of evaporation of perspiration. A period of 10 to 90 minutes would elapse before the next hot flash would occur, both during the daytime and throughout the night. It was common for there to be between 20 to 30, and as many as 40 hot flashes over the course of a day at their peak in frequency, although not all would be of the same intensity.

Treatment was initiated with tizanidine, a non-selective alpha-2-adrenergic agonist, initially for the purpose of providing a sleep aide. Tizanidine is available as a scored 4 mg tablet that can easily be broken into four 1 mg portions. Therefore, the initial dose provided was 1 mg at bedtime, and the dose was raised as needed, every fourth day, to a maximum of 8 mg, if needed, usually at bedtime. However, if the maximum of 8 mg was not taken at bedtime, the patient was permitted to use up to the remaining amount of tizanidine, but not more than a total of 8 mg for the night, if she awoke during the night and found that she could not fall back to sleep. This was not necessary, and once asleep, she was able to sleep through the night waking infrequently but rapidly falling back to sleep.

Safety monitoring included making certain there were no issues with liver function, low blood pressure or unusual dreams as this was accomplished. Tizanidine could, if needed, be dosed again during the night without causing a morning "hangover" effect providing there was a four hour sleep window available.

HRT was not an option for controlling her hot flashes since this woman had been diagnosed with hormone receptor positive breast cancer. She had additional challenges in the potential treatment of hot flashes because of the history of breast cancer. This was in part because she had received chemotherapy which caused a peripheral neuropathy. Consequently, the hot flashes she experienced were perceived with even greater intensity because the overwhelming sense of rising body heat was in direct contrast to the constant freezing cold sensation of the neuropathy felt in both feet. In addition, she was receiving an aromatase inhibitor (anastrozole, 1 mg daily), a medication to block the production of estrogen and progesterone, in effect, anti-HRT. This further exacerbated the hot flashes into "super" hot flashes, a known side effect of this type of medication. For her, the "super" hot flashes were beyond the intensity of her previously experienced menopausal hot flashes. These hot flashes were crippling. They prevented her from functioning normally, required that she bring changes of underwear and clothing to work, interrupted her sleep and interfered with her ability to function in her normal activities of daily living. They impacted her safety and the safety of others as well, regarding her ability to effectively drive and accurately perform her job duties.

Other medication alternatives reported in the medical literature which had partial success in reducing hot flash frequency and severity by as much as 50% were evaluated by titrating to the doses reported, and maintained at those doses for at least a two-week trial. These included clonidine at a dose up to 0.4 mg, gabapentin at a dose of up to 1800 mg and venflaxamine at a dose of up to 300 mg. However, these were not satisfactory in reducing hot flashes by more than 25% in this individual. Therefore, following the unsuccessful trials with these agents the focus was switched to a trial with a novel agent, ropinirole, a dopamine agonist.

With ropinirole, the goal has been directed at regulating GnRH, and controlling the unsuppressed LH pulses characteristic of menopause, through the action on $D_2$ and $D_3$ receptors within the hypothalamus. Prior ineffective dopamine agonists that have been used for this purpose have had opposite actions on these molecules because they worked on the $D_1$ and $D_5$ receptors. The responses of the $D_1$ and $D_5$ receptors vs. the $D_2$, $D_3$ and $D_4$ receptors are diametrically opposed.

Ropinirole titration was initiated with 0.25 mg at bedtime, and if tolerated, by escalating the dose by 0.25 mg every fourth day to a maximum of 1 mg (i.e., 0.25 mg, 0.50 mg, 0.75 mg, 1 mg), until there was reduction in both the frequency and severity of hot flashes. If higher doses were needed, then both 1 mg, or later 2 mg and both 1 and 2 mg ropinirole tablets were used along with the continued titration by 0.25 mg steps every fourth day until a maximum of 4 mg was reached. Higher ropinirole doses were not needed to accomplish clinical suppression of the hot flashes in this woman, and were not tested due to a greater likelihood of side effects such as nausea, hallucinations or jitteriness.

With this protocol it was possible to provide aide to allow this patient to fall asleep within 15 to 20 minutes, rather than tossing and turning for up to two hours before falling asleep. In addition, this patient was able to sleep through the night for seven to eight hours on this treatment, while without treatment she had been awakening anywhere from two to three times per hour once she did fall asleep.

The combination of ropinirole and tizanidine represented a new combination that provided aide in falling asleep, staying asleep and providing significant additional relief by completely eliminating the frequency and severity of hot flashes that this patient had experienced prior to treatment until the next dosing the following evening. This was a highly significant and dramatically notable improvement compared to any prior option available. Ropinirole was shown to reduce hot flashes as a dopamine agonist on the $D_2$, $D_3$ and $D_4$ receptors. The new combination of ropinirole and tizanidine was additionally effective in totally eliminating the most severe form of hot flashes, with the most intense vasomotor symptoms. It completely stopped the frequency and intensity of these symptoms. When the dose of ropinirole was removed, the symptoms returned. When the ropinirole was re-administered at 4 mg, the hot flashes once again disappeared. The duration of relief of the combined ropinirole and tizanidine allowed once a day dosing.

The second woman, JM is a 52-year-old woman with multiple sclerosis (MS) for 26 years. She had been experiencing difficulty with vision, inability to walk due to spinal symptoms, severe neurogenic bladder with incontinence, fatigue and multiple hot flashes throughout the day causing severe sweats and a sensation of heat overcoming her body. Ironically, with the sensation of heat there was an overwhelming sense of weakness and fatigue. This possibly reflected what is known as the "pseudoexacerbation" phenomenon in MS. Central nervous system (CNS) nerve fibers that already are physically damaged, but somewhat physiologically compensated, can lose their ability to compensate as body temperature rises. The function of these nerve fibers can improve once again as body temperature cools.

Patient JM is extremely temperature sensitive and wears a cooling vest to remain on the cool side for this very purpose. Prior to treatment with ropinirole for the regulation of her hot flashes, JM had been experiencing anywhere from 15-20 hot flashes per day, with severe flushing of the face and chest and associated weakness. She attempted to cool herself with a hand held, battery operated fan and by drinking ice cold liquids. While that effort provided some improvement of symptoms by shortening the duration of her hot flash associated weakness, it did not prevent the recurrent episodes. Hormone Replacement Therapy (HRT) was not an acceptable option for her due to her high risk profile for Deep Vein Thrombosis (DVT) because of her immobility due to paralysis from the MS, and her smoking history.

She was using tizanidine for treatment of spasticity and the dose was adjusted to provide 8 mg at bedtime to facilitate sleep, which it did. In addition, she was titrated up to a ropinirole dose of 4 mg daily at bedtime which totally eliminated the vasomotor symptoms (hot flashes) without side effects. The combination of ropinirole and tizanidine provided long duration benefit that allowed once a day dosing. In addition, there was also resolution of the MS pseudoexacerbation phenomenon. The combination of these two agents provided a new product that aided her falling asleep, staying asleep and completely eliminated her hot flashes of menopause, in a circumstance where HRT was contraindicated due to high risk of vascular complications from immobility and smoking (DVT).

The third woman, DH is a 53-year-old woman with multiple peripheral nerve injuries and diabetes. She entered menopause two years ago and developed the menopausal symptom of hot flashes with a frequency of 15-20 hot flashes per day, with each one lasting 15-30 seconds in duration. There was flushing and reddening of the face and the chest, with associated beading of sweat, during these hot flashes and they interfered with her ability to obtain a full night of normal sleep. She had been able to fall asleep with the use of sedative hypnotic medication, temazepam, even prior to the onset of the hot flashes.

After the onset of the hot flashes she noted difficulty sleeping throughout the night because of drenching night sweats associated with the hot flashes after which she would feel very cold. HRT was not an acceptable form of treatment due to metabolic issues with the control of her diabetes. She then received the combination of both tizanidine, titrated up to 8 mg at bedtime, and topinirole, which was also titrated to 4 mg at bedtime as with the other patients. Her sleep improved and her hot flashes completely resolved with once a day dosing of both ropinirole (4 mg) and tizanidine (8 mg) at bedtime with no untoward side effects.

Cessation of the hot flashes, combined with uninterrupted sleep not only leads to a more productive work day, but a safer day as well, regarding such activities as operating an automobile, where alertness is imperative. Her diabetes remained under excellent control.

The fourth woman, PW is a 48-year-old woman with a chronic neuropathic pain disorder who entered menopause at a younger age than most, but developed hot flashes with drenching night sweats as significant symptoms like most. The hot flashes were associated with facial flushing and flushing of the chest. These episodes lasted 15-30 seconds each and would occur 10-15 times per day. She already was under treatment with clonidine, gabapentin and venflaxamine for her neuropathic pain and associated depression, and developed these hot flash symptoms despite those medications. Hormone Replacement Therapy (HRT) was contraindicated because of the potential for worsening her depression. Tizanidine 4 mg was titrated for sleep to 8 mg at bedtime, and treatment with ropinirole was initiated and titrated to 4 mg at bedtime. She slept on and on the ropinirole 4 mg at bedtime she had complete resolution of the frequency and severity of the hot flashes without untoward side effects. She previously had manifested irritability and difficult concentrating which seemed to improve as the hot flashes abated and sleep improved.

The combination of these two agents (ropinirole and tizanidine) represents a new combination that provides aide in falling asleep, staying asleep and providing significant relief by completely eliminating the frequency and severity of hot flashes which were resistant to other medication described as potentially useful in the medical literature. The duration of benefit utilizing this combination allows once daily dosing. HRT would not have been an acceptable alternative for this patient because of the probability of it having a negative impact on her already altered mood state associated with her pain disorder. This new product was effective in totally eliminating her intense vasomotor symptoms (hot flashes), and improving her ability to sleep.

Two of the most incapacitating symptoms of menopause are hot flashes and disruption of the normal sleep pattern. Although there have been many attempts to address each of these symptoms individually, treatment methods thus far do not adequately resolved symptoms, and many have also created additional health risks. Further, no singular product has addressed both of these symptoms. The subject invention describes a novel and new use of a $D_2$ receptor family dopamine agonist to alleviate and control menopausal symptoms in women, and in particular, hot flashes. As a dopamine agonist, ropinirole is believed to bind to the $D_2$, $D_3$, or $D_4$ receptors, particularly at the $D_3$ site. This affinity inhibits production of GnRH which reduces production of LH and FSH in the pituitary. LH and FSH are vasodilators, and lower pulsatile levels of LH and FSH result in reduced incidence of hot flashes.

In another clinical study, a total of six (6) women with dramatic vasomotor hot flashes and sleep disruption were evaluated and treated with either ropinirole (4 mg) (a $D_2$, $D_3$, or $D_4$ dopamine agonist), tizanidine (4 mg) (an alpha-2-adrenergic agonist), clonidine (0.1 mg) (an alpha-2-adrenergic agonist), rotigotine (1 mg) (a $D_2$, $D_3$ or $D_4$ dopamine agonist), pramipexole (1.5 mg) (a $D_2$, $D_3$ or $D_4$ dopamine agonist), or the $D_2$ antagonists chlorpromazine (25 mg) or haloperidol (1 mg) being used as a sedative. Patients were on each regimen at the doses cited for up to four weeks.

Symptoms were evaluated on a scale from 0 to 4, with 0 being not affected, 1 being mild, 2 being moderate, 3 being severe, and 4 being a very severe expression of either vasomotor symptom frequency, severity, sweating, falling asleep and waking during the night for each patient and evaluated at the end of the treatment period. The findings reported are based on an average of the reported symptoms of the six women studied.

Specifically, regarding hot flash frequency, evaluation was based upon the number of hot flashes per day. The frequency of hot flashes was graded on a scale of 0-4, with 0 as none detected, 1 as 1-4/day (mild), 2 as 5-8/day (moderate), 3 as 9-12/day (severe), and 4 as more than 12/day (very severe).

The severity of the hot flashes, reflecting hot flash duration, was also graded on a scale of 0-4, with 0 being not detected, 1 being mild (less than 1 minute), 2 moderate (1-2 minutes), 3 severe (2-3 minutes), and 4 very severe (greater than 4 minutes). This evaluation reflects the duration and intensity as rated by the individual.

The sweating response was graded on a scale of 0-4 as well, with 0 being not detected, 1 being mild (minimally moist skin), 2 moderate (moisture of the skin), 3 severe (noticeable perspiration, hair, ears, neck, chest), and 4 very severe (soaking sweat).

Falling asleep was also graded on a scale of 0-4, with 0 being no issue (less than 15 minutes), 1 being mild (15-20 minutes), 2 moderate (20-40 minutes), 3 severe (40-60 minutes), and 4 very severe (greater than 60 minutes).

Wakings were graded on a scale of 0-4 as well, with 0 being not detected, 1 being mild (1-5 wakings/night), 2 moderate (5-10 wakings/night), 3 severe (10-15 wakings/night), and 4 very severe (greater than 15 wakings/night).

The $D_2$ receptor family ($D_2$, $D_3$ or $D_4$) agonists ropinirole, rotigotine and pramipexole were examined, and contrasted with $D_2$ receptor family antagonists chlorpromazine or haloperidol. Ropinirole and pramipexole were evaluated alone and with either alpha-2-adrenergic agonist tizanidine or clonidine.

Additionally, venlafaxine, paroxetine, gabapentin, and pregabilin interact with and effect $D_2$ receptors and produce affects as $D_2$ agonists. Venlafaxine and paroxetine form heterodimers with the $D_2$ receptors and effectuate a response akin to $D_2$ agonists. Additionally, there are also a number of interactions between gabapentin and pregabalin with the $D_2$ family of receptors which cause a release of dopamine and also include effects on the N-type calcium channel receptors. Venlafaxine, paroxetine, gabapentin, and pregabilin were also evaluated in comparison with tizanidine.

The following chart summarizes the results of the treatments.

| Treatment | Hot Flash Frequency | Hot Flash Severity | Sweating | Falling Asleep | Wakings |
|---|---|---|---|---|---|
| Untreated | 3 | 3 | 3 | 2 | 4 |
| $D_2$ Agonist Group | | | | | |
| Ropinirole | 0 | 0 | 0 | 1 | 1 |
| Rotigitine | 0 | 0 | 0 | 0 | 1 |
| Pramipexole | 0 | 0 | 0 | 0 | 1 |
| Venlafaxine | 2 | 2 | 3 | 2 | 3 |
| Paroxetine | 2 | 2 | 3 | 2 | 2 |
| Gabapentin | 2 | 2 | 3 | 2 | 2 |
| Pregabilin | 2 | 2 | 3 | 2 | 1 |
| Alpha-2-Adrenergic Agonist | | | | | |
| Tizanidine | 2 | 2 | 3 | 0 | 1 |
| Clonidine | 2 | 2 | 3 | 1 | 2 |
| Ropinirole and Tizanidine | 0 | 0 | 0 | 0 | 1 |
| Ropinirole and Clonidine | 0 | 0 | 0 | 0 | 1 |
| Pramipexole and Tizanidine | 0 | 0 | 0 | 0 | 1 |
| Pramipexole and Clonidine | 0 | 0 | 0 | 0 | 1 |
| Venlafaxine and Tizanidine | 2 | 1 | 2 | 0 | 1 |
| Paroxetine and Tizanidine | 2 | 1 | 3 | 0 | 1 |
| Gabapentin and Tizanidine | 1 | 1 | 2 | 0 | 1 |
| Pregabilin and Tizanidine | 1 | 2 | 3 | 0 | 1 |
| $D_2$ Antagonist Group | | | | | |
| Chlorpromazine | 4 | 4 | 4 | 0 | 4 |
| Haloperidol | 4 | 4 | 4 | 0 | 4 |

All six patients experienced very pronounced symptoms without treatment. With ropinirole, rotigotine or pramipexole alone, there was notable reduction in frequency and severity of vasomotor symptoms and reduction of sweating as well. There was limited impact on sleep. With either tizanidine or clonidine alone, there was very modest reduction in vasomotor symptoms, but an impressive effect on sleep. The combination of ropinirole or pramipexole and either tizanidine or clonidine was synergistic, and provided a more robust response. In addition, the duration of effect was greater with the combination of a $D_2$ receptor family agonist and the alpha-2-agonist than use of the $D_2$ agonist alone, so that once daily dosing was possible utilizing the combination. Venlafaxine (75 mg), paroxetine (20 mg), gabapentin (300 mg), and pregabilin (50 mg) also reduced hot flash symptoms over untreated patients. When tizanidine (4 mg) was administered with venlafaxine, paroxetine, gabapentin, and pregabilin, the combination was synergistic and produced a more robust response in the reduction of hot flash symptoms and other vasomotor symptoms.

In contrast, the $D_2$ receptor family antagonists, chlorpromazine or haloperidol aggravated menopausal symptoms, confirming the pivotal role of the $D_2$ receptor family in expression of these symptoms.

In another clinical study, the results of treatment with a combination of a $D_2$, $D_3$, or $D_4$ dopamine agonist and an alpha-2-adrenergic agonist was found to be more beneficial than the cumulative effect of treatment with these compounds individually, thus demonstrating that a $D_2$, $D_3$, or $D_4$ dopamine agonist and alpha-2-adrenergic agonist work together synergistically. In this study, a total of eight (8) women with menopausal vasomotor symptoms and sleep disruption were evaluated and treated with either ropinirole (4 mg) (a $D_2$, $D_3$, or $D_4$ dopamine agonist), tizanidine (4 mg) (an alpha-2-adrenergic agonist), ramelteon (8 mg) (a substance with sedative effects though not classified as a sedative), ropinirole (4 mg)/tizanidine (4 mg), or ropinirole (4 mg)/ramelteon (8 mg) at bedtime. Patients were on each regimen at the doses cited for at least four weeks.

Symptoms were evaluated on a scale from 1 to 4, with 1 being mild, 2 being moderate, 3 being severe, and 4 being a very severe expression of either vasomotor symptom frequency, severity, sweating, falling asleep and wakings during the night were evaluated for each patient and evaluate at the end of the treatment period. The findings were based on an average of the reported symptoms of the eight women studied.

Specifically with respect to hot flash frequency, evaluation was based upon the number of hot flashes per day. The frequency of the hot flashes was graded on a scale of 1-4, with 1 as 1-4/day (mild), 2 as 5-8/day (moderate), 3 as 9-12/day (severe), and 4 as more than 12/day (very severe).

The severity of the hot flashes was graded on a scale of 1-4, with 1 being mild (less than 1 minute), 2 moderate (1-2 minutes), 3 severe (2-3 minutes), and 4 very severe (greater than 4 minutes). This evaluation reflects the duration and intensity as rated by the individual.

The sweating response was graded on a scale of 1-4, with 1 being mild (minimally moist skin), 2 moderate (moisture on skin), 3 severe (noticeable perspiration, hair, ears, neck, chest), and 4 very severe (soaking sweat).

Falling asleep was graded on a scale of 1-4, with 1 being mild (15-20 minutes), 2 moderate (20-40 minutes), 3 severe (40-60 minutes), and 4 very severe (greater than 60 minutes).

Wakings were graded on a scale of 1-4, with 1 being mild (1-5 wakings/night), 2 moderate (5-10 wakings/night), 3 severe (10-15 wakings/night), and 4 very severe (greater than 15 wakings/night).

The following chart summarizes the results of the treatments:

| Treatment | Hot Flash Frequency | Hot Flash Severity | Sweating | Falling Asleep | Wakings |
|---|---|---|---|---|---|
| Untreated | 4 | 4 | 3 | 4 | 3 |
| Ropinirole (4 mg) | 1 | 1 | 1 | 3 | 3 |
| Tizanidine (4 mg) | 3 | 3 | 3 | 2 | 2 |
| Ramelteon (8 mg) | 4 | 4 | 3 | 3 | 3 |
| Ropinirole/Tizanidine | 0 | 0 | 0 | 0 | 1 |
| Ropinirole/Ramelteon | 1 | 2 | 2 | 3 | 3 |

All eight patients experienced very severe symptoms without treatment. With ropinirole alone, there was notable, but incomplete reduction in frequency and severity of vasomotor symptoms and reduction of sweating as well. There was limited impact on sleep. With tizanidine alone, there was very modest reduction in vasomotor symptoms, but a more impressive effect on sleep. The sleep medicine ramelteon had no impact on vasomotor symptoms, and had only a limited impact on sleep in this menopausal patient population. The combination of ropinirole and tizanidine was synergistic, with a more pronounced effect on vasomotor symptoms and sleep than either agent showed when used alone. There was complete elimination of vasomotor symptoms, and significant improvement in the time to fall asleep and significant reduction of wakings. The duration of effect was greater with the combination of a $D_2$ receptor family agonist and alpha-2-agonist than the $D_2$ agonist alone, so once daily dosing was possible utilizing the combination. In contrast, the combination of ropinirole and ramelteon was no better than either agent when used alone.

The invention has been disclosed in terms of preferred embodiments which fulfill all of the objects of the present invention and overcome the limitations of the prior art. Various changes, modifications, and alterations from the teachings of the present invention may be contemplated by those skilled in the art without departing from the intended spirit and scope thereof. It is intended that the present invention only be limited by the terms of the appended claims.

I claim:

1. A method of treatment of hot flashes comprising the steps of:

administering an effective amount of a chemical composition to a person experiencing hot flashes, the composition being a dopamine agonist, other than Ropinrole, capable of binding to $D_2$, $D_3$, and $D_4$ dopamine receptors, and evaluating the effects of administration of the composition.

2. A method of treatment of hot flashes as set forth in claim 1 wherein the method of administration of the chemical composition is selected from the group consisting of administration of the composition in a pill, administration of the composition orally in a liquid form, administration of the composition intravenously in a liquid form, administration of the composition using a transdermal patch, and administration of the composition by inhalation.

\* \* \* \* \*